(12) United States Patent
Kim

(10) Patent No.: US 12,097,281 B1
(45) Date of Patent: Sep. 24, 2024

(54) COMPOSITION FOR IMPROVING SKIN MOISTURIZATION OF COMPANION ANIMALS

(71) Applicant: Tae Yoon Kim, Yangju-si (KR)

(72) Inventor: Tae Yoon Kim, Yangju-si (KR)

( * ) Notice: Subject to any disclaimer, the term of this patent is extended or adjusted under 35 U.S.C. 154(b) by 0 days.

(21) Appl. No.: 18/630,703

(22) Filed: Apr. 9, 2024

(30) Foreign Application Priority Data

Jun. 5, 2023 (KR) .................. 10-2023-0072396

(51) Int. Cl.
| | | |
|---|---|---|
| *A61K 36/00* | (2006.01) | |
| *A61K 8/368* | (2006.01) | |
| *A61K 8/60* | (2006.01) | |
| *A61K 8/73* | (2006.01) | |
| *A61K 8/92* | (2006.01) | |
| *A61K 8/9722* | (2017.01) | |
| *A61K 8/9789* | (2017.01) | |
| *A61K 8/9794* | (2017.01) | |
| *A61K 8/98* | (2006.01) | |
| *A61Q 19/00* | (2006.01) | |

(52) U.S. Cl.
CPC .............. *A61K 8/987* (2013.01); *A61K 8/368* (2013.01); *A61K 8/60* (2013.01); *A61K 8/735* (2013.01); *A61K 8/922* (2013.01); *A61K 8/9722* (2017.08); *A61K 8/9789* (2017.08); *A61K 8/9794* (2017.08); *A61Q 19/007* (2013.01); *A61K 2800/85* (2013.01)

(58) Field of Classification Search
None
See application file for complete search history.

(56) References Cited

FOREIGN PATENT DOCUMENTS

| | | |
|---|---|---|
| KR | 10-1978761 B1 | 5/2019 |
| KR | 10-2007762 B1 | 8/2019 |
| KR | 10-2020-0120422 A | 10/2020 |
| KR | 10-2210112 B1 | 2/2021 |
| KR | 10-2320873 B1 | 11/2021 |
| KR | 10-2420269 B1 | 7/2022 |
| KR | 10-2474794 B1 | 12/2022 |

OTHER PUBLICATIONS

Korean Office Action for related KR Application No. 10-2023-0072396 mailed Jun. 21, 2023 from Korean Intellectual Property Office.
Korean Government, "The Standards and Specifications for Fodder, etc.", Ministry of Agriculture, Food and Rural Affairs Notice, Jul. 22, 2022. pp. 1-576.
Naver et al. "Hyaluronic Acid Sodium Related Data (Well-Known Usage Technique)", 2014, 2019, 2021, 2022, pp. 1-20.
Korean Notice of Allowance for related KR Application No. 10-2023-0072396 mailed Jul. 19, 2023 from Korean Intellectual Property Office.
Korean Office Action for related KR Application No. 10-2023-0072396 mailed Jul. 12, 2023 from Korean Intellectual Property Office.

*Primary Examiner* — Russell G Fiebig
(74) *Attorney, Agent, or Firm* — Paratus Law Group, PLLC

(57) ABSTRACT

A composition for improving skin moisturization of companion animals, including 10 to 20 parts by weight ("wt. parts") of olive oil, 5 to 10 wt. parts of oleanolic acid acetate powder, 30 to 40 wt. parts of barley sprout fermented extract powder, 30 to 40 wt. parts of broccoli sprout fermented extract powder, 5 to 15 wt. parts of coconut extract fine powder, 1.5 to 2.5 wt. parts of sodium hyaluronate purified powder, 5.5 to 10 wt. parts of trehalose powder, 5 to 10 wt. parts of *chlorella* powder, and 5 to 10 wt. parts of green leaf mussel extract powder, based on 100 wt. parts of purified water.

5 Claims, 4 Drawing Sheets

| Division | Start | 4 weeks | 8 weeks | 12 weeks |
|---|---|---|---|---|
| Test dog #1 | 21 | 24 | 28 | 33 |
| Test dog #2 | 27 | 31 | 36 | 38 |
| Test dog #3 | 22 | 23 | 33 | 35 |

| Division | Start of experiment | 4 weeks of experiment | 8 weeks of experiment | End of experiment (12 weeks later) |
|---|---|---|---|---|
| Test dog #1 |  |  |  |  |
| Test dog #2 |  |  |  |  |
| Test dog #3 |  |  |  |  |

COMPOSITION FOR IMPROVING SKIN MOISTURIZATION OF COMPANION ANIMALS

CROSS REFERENCE TO RELATED APPLICATION

This application claims priority to Korean Patent Application No. 10-2023-0072396 (filed on Jun. 5, 2023), which is hereby incorporated by reference in its entirety.

BACKGROUND

The present invention relates to a composition for improving skin moisturization of companion animals, and more particularly, to a composition for improving skin moisturization of companion animals, which induces systemic and local immune response to microbial antigens or antigens, and complex interactions of susceptibility genes through dietary supplements (feeding) including olive oil, oleanolic acid acetate powder, barley sprout fermented extract powder, broccoli sprout fermented extract powder, coconut extract fine powder, sodium hyaluronate purified powder, trehalose powder, *chlorella* powder and green leaf mussel extract powder as active ingredients, so as to increase skin moisturizing effects and to contribute to preventing dermatitis.

Pets refer to animals that people like, keep close to, and protect, and include dogs, cats, birds, goldfish and the like.

Among them, some pets, such as dogs and cats, are expanding their roles as companion animals that live with their owners and share emotional sympathy in a personalized modern society. In recent years, types of the companion animals are diversifying, for example, include parrots, hedgehogs, rabbits and hamsters as well as the dogs and cats, and related industries are also developing rapidly.

For example, food or snacks for companion animals are not simply a means of supplying nutrients, but contain various ingredients to improve the health of the companion animals, as well as products with improved texture or flavor according to preference.

Meanwhile, it has been found that dermatitis occurs in companion animals similarly to the human body, and are the most frequently occurring diseases in the entire population among various diseases.

Skin trouble reactions, that is, diseases and wounds including inflammation or bacteria induce oxidative stress. The oxidative stress attenuates the inflammatory response by promoting the activation of macrophages and the secretion of inflammatory cytokines.

Oxidative substances or oxidants that cause oxidative stress are naturally generated in normal metabolic processes such as the process of using nutrients to produce energy or the immune response to destroy invading bacteria or viruses from an outside.

The oxidants are very unstable, and when produced or accumulated more than necessary, would damage DNA and cells, thereby resulting in detrimental effects such as aging such as melanin and wrinkle formation, chronicity and deterioration of inflammation, and delayed wound healing.

The presence of an antioxidant system plays a role in removing oxidants in the body during this process. Most skin inflammations are caused by microbial infection, and when bacteria invade the body, histamine, prostaglandin, and leukotriene, etc. are locally released to the infected area to defend against microorganisms, resulting in inducing symptoms such as fever, redness, pain, swelling, etc.

When cytokines such as nitric oxide (NO), tumor necrosis factor (TNF-αt) and interleukin 6 (IL-6) are excessively produced during the inflammatory response of macrophages, the intracellular antioxidant defense system is weakened.

Accordingly, antioxidant enzyme activity is reduced and oxidative stress is rapidly increased. Therefore, defending against oxidative stress in skin trouble can be suggested as a primary improvement and a way to prevent skin troubles, and there is a trend that interest in antioxidants helpful for prevention of inflammatory reactions and oxidative stress is steadily increasing.

PRIOR ART LITERATURE

Patent Document

Korean Patent Registration No. 10-2320873, Composition for improving companion animal skin and fur Korean Patent Registration No. 10-2474794, Animal feed additive for improving atopic skin disease containing medicinal herb complex extract and manufacturing method thereof Korean Patent Registration No. 10-2420269, Health functional food composition for improving skin health of the companion animals Korean Patent Registration No. 10-2210112, Composition for improving and treating hair loss, hair damage and skin diseases in animals, which contains vitamin C as an active ingredient Korean Patent Registration No. 10-2007762, Composition for managing companion animal skin and hair Korean Patent Registration No. 10-2420269, Health functional food composition for improving skin health of the companion animals

SUMMARY

The present invention was created to review and solve such various problems in the prior art as described above, and a main object of the present invention is to provide a composition for improving skin moisturization of companion animals, which induces systemic and local immune responses to microbial antigens and antigens, and complex interactions of susceptibility genes through dietary supplements including olive oil, oleanolic acid acetate powder, barley sprout fermented extract powder, broccoli sprout fermented extract powder, coconut extract fine powder, sodium hyaluronate purified powder, trehalose powder, *chlorella* powder and green leaf mussel extract powder, as active ingredients, so as to increase skin moisturizing effects and to contribute to prevention of dermatitis.

As a means for achieving the above object, the present invention provides a composition for improving skin moisturization of companion animals, which includes 10 to 20 parts by weight ("wt. parts") of olive oil, 5 to 10 wt. parts of oleanolic acid acetate powder, 30 to 40 wt. parts of barley sprout fermented extract powder, 30 to 40 wt. parts of broccoli sprout fermented extract powder, 5 to 15 wt. parts of coconut extract fine powder, 1.5 to 2.5 wt. parts of sodium hyaluronate purified powder, 5.5 to 10 wt. parts of trehalose powder, 5 to 10 wt. parts of *chlorella* powder, and 5 to 10 wt. parts of green leaf mussel extract powder, based on 100 wt. parts of purified water.

According to the present invention, it is possible to induce systemic and local immune responses to microbial antigens and antigens, and complex interactions of susceptibility genes through dietary supplements including olive oil, oleanolic acid acetate powder, barley sprout fermented extract powder, broccoli sprout fermented extract powder, coconut extract fine powder, sodium hyaluronate purified powder, trehalose powder, *chlorella* powder and green leaf mussel extract powder, as active ingredients, thereby attaining improved effects such that skin moisturizing effects are increased to contribute to prevention of dermatitis.

BRIEF DESCRIPTION OF THE DRAWINGS

The above and other objects, features and other advantages of the present invention will be more clearly understood from the following detailed description taken in conjunction with the accompanying drawings, in which.

DETAILED DESCRIPTION

Figures 1, 2:
FIG. 1 is photographs illustrating a process of measuring skin moisture using Belulu water content measurement instrument.
FIG. 2 is a photograph illustrating a measured result displayed on the Belulu water content measurement instrument and a table illustrating the measured values (% unit) of skin moisture.

Hereinafter, preferred embodiments of the present invention will be described in detail with reference to the accompanying drawings.

Prior to the description of the present invention, the following specific structural or functional descriptions are only exemplified for the purpose of describing embodiments according to the concept of the present invention, and such embodiments according to the concept of the present invention may be implemented in various forms, and should not be construed as being limited to the embodiments described herein.

The composition for improving skin moisturization of companion animals according to the present invention may include olive oil, oleanolic acid acetate powder, barley sprout fermented extract powder, broccoli sprout fermented extract powder, coconut extract fine powder, sodium hyaluronate purified powder, trehalose powder, *chlorella* powder and green leaf mussel extract powder, as active ingredients.

Therefore, this composition may be soaked in purified water and made in a tablet form to be fed to companion animals, especially puppies.

More specifically, the composition according to the present invention may include 10 to 20 wt. parts of olive oil, 5 to 10 wt. parts of oleanolic acid acetate powder, 30 to 40 wt. parts of barley sprout fermented extract powder, 30 to 40 wt. parts of broccoli sprout fermented extract powder, 5 to 15 wt. parts of coconut extract fine powder, 1.5 to 2.5 wt. parts of sodium hyaluronate purified powder, 5.5 to 10 wt. parts of trehalose powder, 5 to 10 wt. parts of *chlorella* powder, and 5 to 10 wt. parts of green leaf mussel extract powder, based on 100 wt. parts of purified water.

Here, the olive oil is a vegetable oil obtained from olive fruit and contains abundant antioxidants and monounsaturated fatty acids, which are helpful for protecting and maintaining the skin. In particular, it may reduce oxidative stress to facilitate maintaining the moisture and elasticity of the skin, and may also have the function of strengthening the skin barrier thus to facilitate skin moisturization, inhibiting dryness, and maintaining elastic skin. Therefore, the olive oil may be added to contribute to moisturizing the skin of the companion animal.

Further, oleanolic acid in the oleanolic acid acetate is a colorless acicular crystal with a melting point of 310° C. and is a type of treterpene with an oleanine skeleton. This was originally separated from olive leaves, and is now distributed broadly in plant kingdoms such as East Asian swertia, *Eugenia* jammos, *Gentiana lutea* or the like. Alternatively, it is often included as saponin combined with acetic acid derivatives and sugars. It may be extracted from different foods such as olives, soybean extracts, grape skin extracts, and ericium *erinaceus* mushrooms, etc. Further, it is possibly artificially produced by activating insect cells or yeast using the gene CYP716A12, which is involved in the synthesis of oleanolic acid in leguminous plants, and using the similar gene CYP716A17 in grapes. This component has anti-inflammatory, anti-oxidant and wrinkle-improving effects, thereby preventing inflammation occurring in the skin of the companion animals and protecting an occurrence of wrinkles.

Further, the barley sprout fermented extract may be prepared and used as powder by soaking barley sprout for 3-4 hours in a state where 50 to 60 wt. parts of the barley sprout is mixed with 100 wt. parts of purified water, steaming the soaked mixture for 3 hours, then, after cooling to room temperature, placing the treated product in a fermentation room and adding aerobic microorganisms, followed by fermentation for 3 days and then drying and pulverizing the same.

Such barley sprout fermented extract increases the absorption and metabolic available rate of calcium, phosphorus, potassium, zinc, iron, magnesium, etc., prevents skin deposition of the companion animal, suppresses skin itching. Further, as antioxidants, large amounts of beta-carotene, flavonol glycoside rutin, selenium, crystalline polypeptide glutathione, and quercetin are contained to contribute to suppressing skin rashes of the companion animal.

Further, the broccoli sprout fermented extract may be prepared and used as powder by steaming broccoli sprout for 2 hours in a state where 40 to 50 wt. parts of the broccoli sprout is mixed with 100 wt. parts of purified water, then, after cooling to room temperature, immersing the treated product in diluted water containing vanadium ions and water which are diluted at a weight ratio of 1:1000 for 40 to 60 minutes, taking out and placing the treated product in a fermentation room and adding aerobic microorganisms, followed by fermentation for 2 days and then drying and pulverizing the same.

At this time, the reason for using diluted water is to absorb vanadium, which is a natural mineral and nutrient, and is harmless to companion animals, into broccoli and fermented so that the companion animals can consume it, thereby enhancing vascular health of the companion animals and intruding inhibition of dermatitis, soothing and astringent effects.

In addition, the broccoli sprout fermented extract contains large amounts of beta-carotene, flavonol glycoside rutin, selenium, crystalline polypeptide glutathione, and quercetin, which are antioxidants, thus to contribute to suppressing skin rashes of the companion animal.

Further, the coconut extract has anti-inflammatory properties that help fighting with bacteria, viruses and other pathogens, smoothly supply moisture to maintain skin moisture and protect the skin from skin damage due to free radicals, and contribute to reducing wrinkles, such that it is characterized by contributing to skin soothing, moisturizing and maintaining luster of the companion animals.

Further, the sodium hyaluronate is a chiarogel, which is mainly used as an eye drop or for improving arthritis, however, in the present invention, it is added in a small amount to increase a water storage capacity in the dermal layer of the skin so as to enhance the skin moisturizing power of the companion animals.

Further, the trehalose is a disaccharide composed of two glucoses and is a natural substance that binds to water in order to prevent water loss in plants and enables them to have a moisturizing function. The trehalose is included in resurrection plants, *Mourera fluviatilis*, mushrooms, seaweeds, insects, invertebrates, etc., and plays an important role in enabling these organisms to have drying resistance even in harsh environments such as drying or freezing injury. Further, it has osmotic pressure control, moisturizing and anti-crystallization properties. The way of trehalose in plants to protect cells is to protect cell membranes by hydrogen bonding with proteins on the cell surface, and stabilizes the structure of phospholipid membranes to prevent destruction of the lamellar structure of phospholipid membranes due to changes in temperature.

Further, the *chlorella* is a type of plankton, which is powdered and used. It is rich in vitamins and minerals and especially contains carotenoids, which are antioxidants. Therefore, this component has properties of soothing the companion animal's skin due to removal of skin wastes and detoxification function, suppressing inflammation and keeping the skin shiny, that is, in a wet state, as well as improving immunity.

Further, the green leaf mussel extract contains large amount of omega 3, fatty acid chondroitin, and sulfate, such that this extract helps to soothe skin and produce collagen, thereby making the skin shiny and elastic.

Meanwhile, the composition for improving skin moisturization of companion animals of the present invention may further include: 5 wt. parts of rosehip powder, 5 wt. parts of finger root extract powder, 5 wt. parts of artichoke extract powder, and 5 wt. parts of black soybean peptide based on 100 wt. parts of the composition for improving skin moisturizing of the companion animals.

Here, the rosehip powder is powdered fruit of wild rose, has the highest vitamin C content, is rich in minerals such as calcium, magnesium, and iron, etc., and is rich in antioxidants such as oleic acid, palmitic acid, and gamma linolenic acid. Thus, this component contributes to maintaining the luster of the companion animal's skin and suppressing skin inflammation.

Further, the finger root extract powder contains a large amount of panduratin component, which activates a protein component called AMPK to promote lipolysis, whereby it has the greatest effect of suppressing obesity, but also maintains skin elasticity, soothes skin, and reduces inflammation. Furthermore, it has also been reported to have inhibitory effect on inflammation.

In addition, the artichoke extract is rich in cinarin component and vitamins C and E, therefore, may decrease cholesterol in blood vessels and lower triglyceride levels in blood vessels to improve blood vessel health, thereby activating skin, brightening skin tone, and making it shiny.

Further, the black soybean peptide contains glycitein, which contributes to the removal of skin wastes, inhibition of skin discoloration, and maintenance of skin elasticity.

Further, when preparing the finger root extract powder, 5.5 wt. parts of magnesium stearate, 2.5 wt. parts of silicon dioxide, 1.5 wt. parts of niacin, 5 wt. parts of glycosaminoglycan, 5 wt. parts of polygamma glutamic acid and 5 wt. parts of beta-carotin may further be added and mixed, based on 100 wt. parts of the finger root extract powder, thus to produce the extract powder.

At this time, the magnesium stearate is added to contribute to improving skin moisturizing properties and maintaining skin elasticity.

Further, the silicon dioxide serves as a humectant that regulates the amount of moisture in the skin and improves skin lubrication.

In addition, the niacin participates in the production of neurotransmitters and the maintenance of moisture in the skin.

Moreover, the glycosaminoglycans may be obtained from sea squirt extract, which is a long, unbranched polysaccharide, consisting of a repeated structure of disaccharides with added sulfate group, and the repeating unit is composed of amino sugar and urondose or galactose except for keratin, such that it keeps the hair roots strong and elastic, and activates the skin around the hair roots to contribute to maintaining the health of the surface layer by radiance and moisture.

In addition, poly-gamma-glutamic acid is a polymer in which D,L-glutamic acid is combined with gamma-glutamyl, and is a mucous substance produced by microorganisms. Such poly-gamma glutamic acid has excellent dermal regeneration and is effective in maintaining skin moisturization and skin elasticity.

On the other hand, in the present invention, in order to improve supplements, i.e., feedability, 2.5 wt. parts of *stevia*, 2.5 wt. parts of glutathione, 2 wt. parts of erythorbic acid, and 2.5 wt. parts of citric acid may further be added based on 100 wt. parts of the composition for improving skin moisturization of companion animals thus to be formulated as tablets.

At this time, since *stevia* is a natural sweetener, unlike sugar, it only produces sweetness and does not contain sugar, such that this substance is intended to induce preference for feeding while suppressing obesity of the companion animals.

Further, the glutathione is composed of three peptides, glutamic acid, cysteine and glycine, and cycles of oxidation and reduction are repeated to remove toxic peroxides and have excellent antioxidant effects, such that it has the advantage of performing a natural antibiotic function without using antibiotics.

Further, the erythorbic acid enhances the function as an antioxidant.

In addition, the citric acid as an organic acid is added to function as a rancidity inhibitor and a preservative.

Hereinafter, examples will be described.

Example 1

First, the composition for improving skin moisturization of companion animals according to the present invention was prepared as follows, and then soaked in purified water to form a formulation in a tablet form so that it could be fed to companion animals, especially puppies.

That is, based on 100 wt. parts of purified water, 15 wt. parts of olive oil, 8 wt. parts of oleanolic acid acetate powder, 35 wt. parts of barley sprout fermented extract powder, 35 wt. parts of broccoli sprout fermented extract powder, 10 wt. parts of coconut extract fine powder, 2 wt. parts of sodium hyaluronate purified powder, 7 wt. part of trehalose powder, 6 wt. parts of *chlorella* powder, and 8 wt. parts of green leaf mussel extract powder were mixed together to form a formulation in a tablet form.

Example 2

The same procedure as in Example 1 was conducted, except that the barley sprout fermented extract powder was prepared and used by soaking barley sprout for 3-4 hours in a state where 60 wt. parts of the barley sprout is mixed with 100 wt. parts of purified water, and steaming the soaked mixture for 3 hours, then, after cooling to room temperature, placing the treated product in a fermentation room and adding aerobic microorganisms, followed by fermentation for 3 days and then drying and pulverizing the same.

Example 3

The same procedure as in Example 2 was conducted, except that the broccoli sprout fermented extract was prepared and used as powder by steaming broccoli sprout for 2 hours in a state where 50 wt. parts of the broccoli sprout is mixed with 100 wt. parts of purified water, then, after cooling to room temperature, immersing the treated product in diluted water containing vanadium ions and water which are diluted at a weight ratio of 1:1000 for 50 minutes, taking out and placing the treated product in a fermentation room and adding aerobic microorganisms, followed by fermentation for 2 days and then drying and pulverizing the same.

Example 4

The same procedure as in Example 3 was conducted, except that 5 wt. parts of rosehip powder, 5 wt. parts of finger root extract powder, 5 wt. parts of artichoke extract powder, and 5 wt. parts of black soybean peptide were further added, based on 100 wt. parts of the composition for improving skin moisturization of companion animals.

Example 5

The same procedure as in Example 4 was conducted, except that, when preparing the finger root extract powder, 5.5 wt. parts of magnesium stearate, 2.5 wt. parts of silicon dioxide, 1.5 wt. parts of niacin, 5 wt. parts of glycosaminoglycan and 5 wt. parts by weight of polygamma glutamic acid were further added and mixed, based on 100 wt. parts of the finger root extract powder, thus to produce and use the powder.

Example 6

The same procedure as in Example 5 was conducted, except that 2.5 wt. parts of *stevia*, 2.5 wt. parts of glutathione, 2 wt. parts of erythorbic acid, and 2.5 wt. parts of citric acid were further added, based on 100 wt. parts of the composition for improving skin moisturization of companion animals.

Then, the oral administration safety of the tablets of [Examples 1-6] prepared as described above was assessed.

The oral administration safety assessment was performed by evaluating the average change in the weight, feed intake, water intake, skin and whether or not respiratory problems occur for the six examples while feeding the composition of the present invention (Examples 1-6). In order to apply it to oral administration, the composition was processed in a tablet form with microcrystalline cellulose at a final mixing ratio of 1:1 in an easy-to-ingest form, and experiments were conducted for 6 weeks with feeding once a day. The experimental subjects were divided into a control group, a clinical dose group, and a clinical dose 3-fold group for 6 adult 6-year-old pet dog beagles, and tested for changes in weight while feeding the tablets of Examples 1-6, respectively. The same living environment conditions were set, and experiment results are shown in Table 1.

[Evaluation of Changes in Weight]

TABLE 1

| Division | Body weight (kg) (body weight after intake) | | | | | |
|---|---|---|---|---|---|---|
| | 1 week | 2 weeks | 3 weeks | 4 weeks | 5 weeks | 6 weeks |
| Control group | 11.52 | 11.54 | 11.64 | 11.72 | 11.82 | 11.87 |
| 160 mg/kg | 10.78 | 10.77 | 10.76 | 10.81 | 10.85 | 10.92 |
| 480 mg/kg | 12.63 | 12.62 | 12.61 | 12.68 | 12.70 | 12.72 |

As shown in Table 1, in the case of the control group according to the feeding of the composition of the present invention, the initial body weight was observed as 11.52 kg while having 11.87 kg at the end of the experiment. Further, for the clinical dose group (160 mg/kg), it was confirmed to have 10.78 kg at the beginning and 10.92 kg at the end, and for the clinical dose 3-fold group (480 mg/kg), it was confirmed to have 12.63 kg at the beginning and 12.72 kg at the end.

That is, rapid weight change or abnormal symptoms according to the feeding of the composition of the present invention were not found in all of the control group, clinical dose group, and clinical dose 3-fold group, therefore, the composition of the present invention was determined to be safe.

[Evaluation of Feed Intake]

TABLE 2

| Division | Body weight (kg) (body weight after intake) | | | | | |
|---|---|---|---|---|---|---|
| | 1 week | 2 weeks | 3 weeks | 4 weeks | 5 weeks | 6 weeks |
| Control group | 237 | 241 | 232 | 235 | 231 | 236 |
| 160 mg/kg | 231 | 232 | 247 | 235 | 233 | 242 |
| 480 mg/kg | 234 | 236 | 237 | 230 | 235 | 231 |

In the case of feed intake, the control group was observed to have 260 g at the beginning and 265 g at the end of the experiment, and the clinical dose group was observed to have 231 g at the beginning and 242 g at the end. Further, the clinical dose 3-fold group was confirmed to have 234 g at the beginning and 231 g at the end. Further, in the case of feed intake, it was determined that there is no significant decrease compared to the control group even in the clinical dose 3-fold group. That is, rapid changes in feed intake or abnormal symptoms according to the feeding of the composition of the present invention were not found in all of the control group, clinical dose group, and clinical dose 3-fold group.

[Evaluation of Trend for Amount of Drinking Water]

TABLE 3

| Division | Body weight (kg) (body weight after intake) | | | | | |
|---|---|---|---|---|---|---|
| | 1 week | 2 weeks | 3 weeks | 4 weeks | 5 weeks | 6 weeks |
| Control group | 510 | 500 | 505 | 500 | 510 | 495 |
| 160 mg/kg | 440 | 451 | 445 | 455 | 449 | 446 |
| 480 mg/kg | 430 | 437 | 440 | 442 | 440 | 438 |

In the case of the amount of drinking water, about 595 ml was observed at the end of the experiment while having 610 ml at the beginning for the control group. For the clinical dose group, it was confirmed to have 440 ml at the beginning and 446 ml at the end. In addition, for the clinical dose 3-fold group, it was confirmed to have 430 ml at the beginning and 438 ml at the end. Therefore, it was confirmed that the amount of drinking water also did not shown a significant change compared to the control group. In addition, skin, respiratory, behavior, etc. were evaluated for abnormal symptoms, but no significant abnormal symptoms were found.

[Evaluation of Skin Respiratory]

TABLE 4

| Division | Body weight (kg) (body weight after intake) | | | | | |
|---|---|---|---|---|---|---|
| | 1 week | 2 weeks | 3 weeks | 4 weeks | 5 weeks | 6 weeks |
| Control group | Good | Good | Good | Good | Good | Good |
| 160 mg/kg | Good | Good | Good | Good | Good | Good |
| 480 mg/kg | Good | Good | Good | Good | Good | Good |

As a result of the experiment, no rapid decrease or increase in body weight caused by oral administration of the composition of the present invention was observed, or abnormal changes in food intake, and abnormal changes in amount of drinking water were not found. Further, skin rash, dyspnoea, pathogenesis, and abnormal behavior due to stress were not observed.

Further, the safety of oral administration was evaluated by analyzing hematology parameters such as white blood cell (WBC), red blood cell (RBC), and platelet (PLT) counts, and blood chemistry parameters such as glucose (GLC), blood urea nitrogen (BUN), and albumin (ALB) levels. Results thereof are shown in Table 5 below. Further, the change is expressed as an average value while feeding Examples 1-6 for each pet dog.

TABLE 5

| | White blood cell count (0 mg/kg) | |
|---|---|---|
| Division | 1 week | 6 weeks |
| Control group | 10.6 | 10.5 |
| 160 mg/kg | 10.8 | 10.4 |
| 480 mg/kg | 8.5 | 9.8 |
| | Glucose level (0 mg/kg) | |
| Division | 1 week | 6 weeks |
| Control group | 86 | 87 |
| 160 mg/kg | 89 | 82 |
| 480 mg/kg | 86 | 85 |

TABLE 5-continued

| | Red blood cell count (0 mg/kg) | |
|---|---|---|
| Division | 1 week | 6 weeks |
| Control group | 9.3 | 9.4 |
| 160 mg/kg | 9.4 | 9.6 |
| 480 mg/kg | 9.3 | 8.5 |
| | Blood urea nitrogen level (0 mg/kg) | |
| Division | 1 week | 6 weeks |
| Control group | 21.5 | 17 |
| 160 mg/kg | 19.3 | 13.4 |
| 480 mg/kg | 13.5 | 17.3 |
| | Platelet count (0 mg/kg) | |
| Division | 1 week | 6 weeks |
| Control group | 228 | 219 |
| 160 mg/kg | 300 | 298 |
| 480 mg/kg | 310 | 331 |
| | Albumin level (0 mg/kg) | |
| Division | 1 week | 6 weeks |
| Control group | 3.5 | 3.3 |
| 160 mg/kg | 3.35 | 3.25 |
| 480 mg/kg | 3.3 | 3.1 |

As shown in Table 5, as a result of observing changes in white blood cell count, red blood cell count, platelet count, etc. through hematological analysis, all of the values were determined to be within the normal range and no significant abnormal results were observed. Although the glucose levels, blood urea nitrogen levels, and albumin levels were tested to assess liver, kidney and internal organ abnormalities through blood chemistry analysis, no enzyme changes were observed in the kidneys, hepatobiliary system, and internal organs. Therefore, it was determined that there is no problem with oral administration of the composition of the present invention.

Meanwhile, the composition according to the present invention was fed to puppies, and target dogs were selected for an experiment to determine on whether or not skin was moisturized (moisture evaluation, oil content evaluation, contact microscopy evaluation). For experimental dogs 1, 2 and 3 selected as the target dogs, with consent of the owners of dogs, the dogs aged 6-8 years were selected as shown in Table 6 below.

TABLE 6

| Division | Test dog 1 | Test dog 2 | Test dog 3 |
|---|---|---|---|
| Breed | Chocolate poodle | Brown poodle | Yorkshire terrier |

At this time, the beauty expenses at the beginning of the experiment and the beauty expenses 12 weeks after the end of the experiment were supported, and the skin and fur after beauty treatment were photographed and analyzed in the following method.

Further, the feed fed to the experimental dogs was limited to the same feed, and the feeding of separate food possibly become a variable was also limited.

For comparison, firstly, after each 4-week period without feeding the composition of the present invention (tablets of Examples 1-6), the composition of the present invention was administered twice a day (9:00 am and 3:00 pm) to test dog 1, test dog 2 and test dog 3, which were mixed with microcrystalline cellulose at a final mixing ratio of 1:1 and fed in the form of tablets for 12 weeks. Using a skin oil and moisture content (belulu) measurement instrument and a contact microscope 1000× (Smartoi digital microscope, Shenzhen Microlong Technology), skin hairs of test dog 1, test dog 2 and test dog 3 were photographed at an interval of 4 weeks before and after feeding the composition of the present invention.

At this time, with regard to the feeding, the tablets of Examples 1 and 2 were fed to the test dog 1, the tablets of Examples 3 and 4 were fed to the test dog 2, while the tablets of Examples 5 and 6 were fed to the test dog 3.

Further, a specific color of the captured image was selected, and pixel values were extracted with an image analysis program (image pro plus 7.01).

Further, based on the analyzed pixel values, the above values were used as data for assessment of hair gloss improvement, and the pixel values and the hair gloss extent were determined to be proportional.

Figure 3:
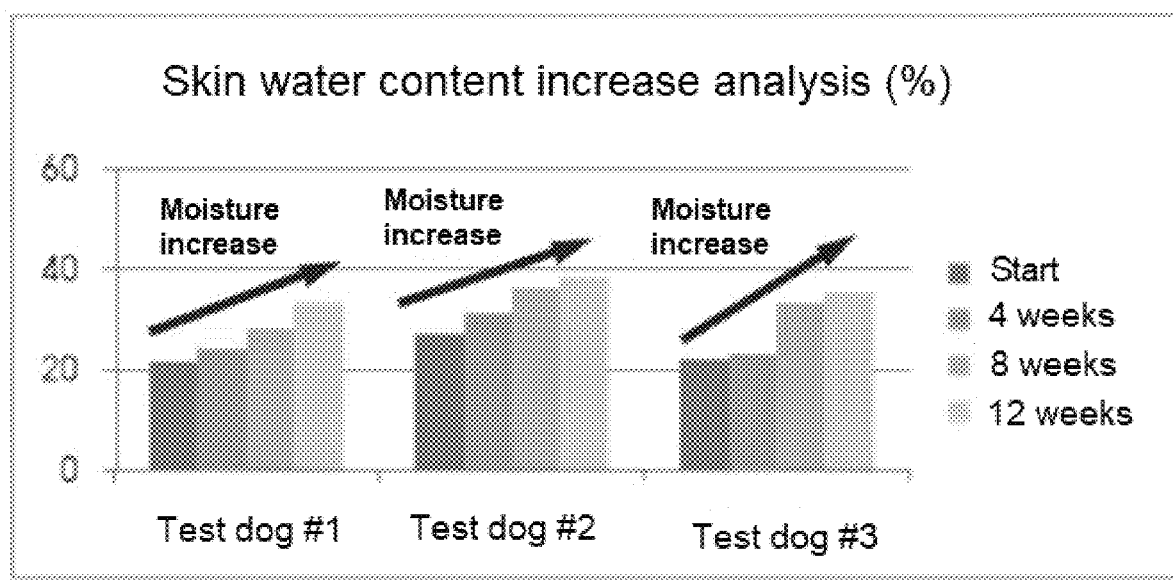
FIG. 3 is a graph illustrating analysis results of skin water content in test dogs over time.

As a result of the experiment, it was confirmed that the skin moisture was increased as shown in FIGS. 1 to 3. Specifically, FIG. 1 is photographs illustrating a process of measuring skin moisture using Belulu water content measurement instrument, FIG. 2 is a photograph illustrating a measured result displayed on the Belulu water content measurement instrument and a table illustrating the measured values (% unit) of skin moisture, and FIG. 3 is a graph illustrating analysis results of skin water content in test dogs over time. From FIG. 3, it can be seen that the skin moisture in all test dogs are increased 12 weeks after the end of the experiment compared to the start of the experiment.

Further, it was confirmed that skin oil content also increased as shown in Table 7 below.

TABLE 7

| Belulu oil content analysis (% unit) | | | | |
| --- | --- | --- | --- | --- |
| Division | Start | 4 weeks | 8 weeks | 12 weeks |
| Test dog #1 | 23 | 24 | 26 | 29 |
| Test dog #2 | 24 | 25 | 29 | 31 |
| Test dog #3 | 23 | 27 | 30 | 32 |

Figure 4:
FIG. 4 is photographs illustrating a process of skin hair observation assessment using contact microscope 1000× shooting in a test dog.
Figure 5:
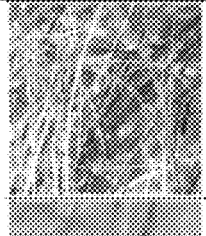
FIG. 5 is Shenzhen Microlong photographs taken with the contact microscope 1000× for skin and hair observation and assessment according to dogs feeding of the composition according to the present invention.
Figure 5:
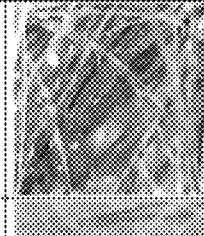
Figure 5:
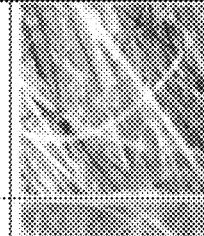
Figure 5:
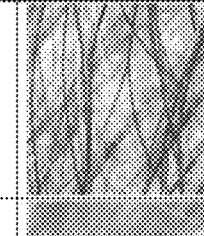
Figure 5:
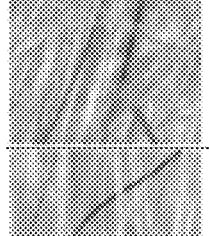
Figure 5:
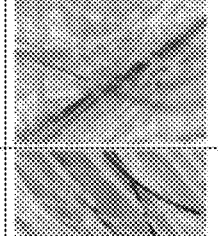
Figure 5:
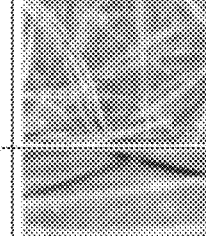
Figure 5:
Figure 5:
Figure 5:
Figure 5:
Figure 5:

Further, in regard to skin hair observation assessment according to the dog feeding of the composition according to the present invention, a process of skin hair observation assessment using contact microscope 1000× shooting in a test dog is shown in FIG. 4, and the contact microscope 1000× shooting Shenzhen Microlong photographs are attached in FIG. 5.

However, FIG. 5 shows photographs taken for test dog 1 fed with Example 1, for test dog 2 fed with Example 3, and for test dog 3 fed with Example 5, respectively.

As shown in FIG. 5, significant visual identification of: (1) alleviation of red rash on the skin of test dogs; (2) reduction of dead skin cells; and (3) improvement of skin and hair gloss, and the like were observed during visual evaluation on the basis of contact microscope shooting 1000×.

Accordingly, it was possible to significantly determine the effects of improving skin moisturization of companion animals by the feeding of [Examples 1-6], which are the composition according to the present invention.

Briefly, considering the improvement measurement value according to the feeding of the composition of the present invention and with reference to assessment of safety such as oral administration safety evaluation (changes in weight, changes in feed intake, changes in amount of drinking water, abnormal behavior), oral administration safety evaluation (hematology WBC, RBC and PLT analyses, and blood chemistry GLC, BUN and ALB analyses), etc., the composition of the present invention can be consistently administered orally to the companion animals. Further, when companion animal's skin moisture evaluation, oil evaluation, evaluation through contact microscopy observation and evaluation of indicators are considered, it was determined that significant improvement can be achieved in regard to moisturizing the companion animal's skin.

What is claimed is:

1. A composition for improving skin moisturization of companion animals, the composition comprising 10 to 20 parts by weight ("wt. parts") of olive oil, 5 to 10 wt. parts of oleanolic acid acetate powder, 30 to 40 wt. parts of barley sprout fermented extract powder, 30 to 40 wt. parts of broccoli sprout fermented extract powder, 5 to 15 wt. parts of coconut extract fine powder, 1.5 to 2.5 wt. parts of sodium hyaluronate purified powder, 5.5 to 10 wt. parts of trehalose powder, 5 to 10 wt. parts of *chlorella* powder, and 5 to 10 wt. parts of green leaf mussel extract powder, based on 100 wt. parts of purified water, thereby forming 100 wt. parts of the composition for improving skin moisturization of companion animals, further comprising 5 wt. parts of rosehip powder, 5 wt. parts of finger root extract powder, 5 wt. parts of artichoke extract powder, and 5 wt. parts of black soybean peptide, based on the 100 wt. parts of the composition for improving skin moisturization of companion animals, wherein the finger root extract powder further comprises 5.5 wt. parts of magnesium stearate, 2.5 wt. parts of silicon dioxide, 1.5 wt. parts of niacin, 5 wt. parts of glycosaminoglycan and 5 wt. parts by weight of polyg-amma glutamic acid, based on 100 wt. parts of the finger root extract powder.

2. The composition according to claim 1, wherein the barley sprout fermented extract powder is prepared by soaking barley sprout for 3-4 hours in a state where 50 to 60 wt. parts of the barley sprout is mixed with 100 wt. parts of purified water, steaming the soaked mixture for 3 hours, then, after cooling to room temperature, placing the treated product in a fermentation room and adding aerobic microorganisms, followed by fermentation for 3 days and then drying and pulverizing the same.

3. A tablet comprising the composition according to claim 1.

4. The tablet according to claim 3, wherein the tablet further comprises microcrystalline cellulose.

5. A method of improving skin moisturization of companion animals, comprising orally administering the tablet according to claim 4 to a companion animal.

* * * * *